United States Patent [19]
Duflos et al.

[11] Patent Number: 6,127,377
[45] Date of Patent: Oct. 3, 2000

[54] VINCA ALKALOID ANTIMITOTIC HALOGENATED DERIVATIVES

[75] Inventors: Alain Duflos; Jacques Fahy, both of Labruguiere; Valérie Thillaye du Boullay, Montans; Jean-Marc Barret; Bridget Hill, both of Castres, all of France

[73] Assignee: Adir et Compagnie, Courbevoie, France

[21] Appl. No.: 09/402,678

[22] PCT Filed: Apr. 10, 1998

[86] PCT No.: PCT/FR98/00730

§ 371 Date: Oct. 7, 1999

§ 102(e) Date: Oct. 7, 1999

[87] PCT Pub. No.: WO98/45301

PCT Pub. Date: Oct. 15, 1998

[30] Foreign Application Priority Data

Apr. 10, 1997 [FR] France ................................. 97 04398

[51] Int. Cl.[7] ........................ A61K 31/475; C07D 519/04; A61P 37/90
[52] U.S. Cl. .......................... 514/283; 514/183; 540/478; 546/52; 546/199
[58] Field of Search ............................ 540/478; 546/52, 546/199; 574/183, 283

[56] References Cited

FOREIGN PATENT DOCUMENTS 2707988  1/1995  France .

OTHER PUBLICATIONS

Fahy, J., JACS 119, No. 36, pp. 8576–8577 (Sep. 10, 1997).

*Primary Examiner*—Evelyn Mei Huang
*Attorney, Agent, or Firm*—The Firm of Gordon W. Hueschen

[57] ABSTRACT

The invention concerns novel halogenated derivatives of the vinblastine and vinorelbine family, corresponding to general formula (I) and their therapeutically acceptable salts. The invention also concerns the application of these compounds in therapy and their method of preparation. The invention further concerns a novel method for preparing vinflunine or 20',20'-difluoro-3',4'-dihydrovinorelbine, of formula (a).

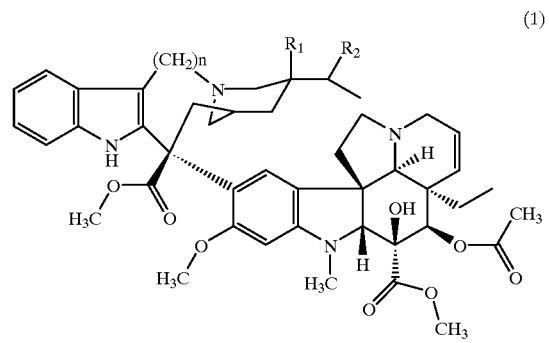

(1)

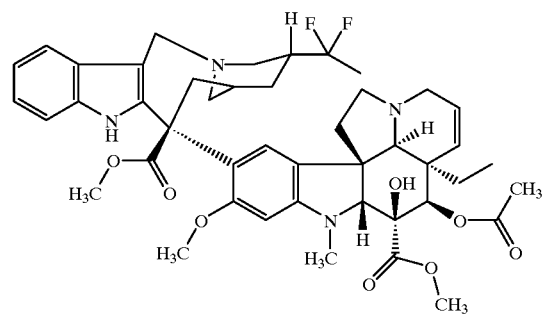

(a)

16 Claims, No Drawings

VINCA ALKALOID ANTIMITOTIC HALOGENATED DERIVATIVES

The present application is a U.S. National Application filed under 35 USC 371 of PCT/FR98/00730, filed Apr. 10, 1998 based upon French application Ser. No. 97 04398 filed Apr. 10, 1997.

The dimeric alkaloids of *Catharanthus roseus* and their derivatives, commonly referred to as Vinca alkaloids, have been widely used in anticancer chemotherapy for about thirty years. They are represented by four products:

two natural compounds: vinblastine and vincristine, two semisynthetic products: vindesine, obtained from vinblastine, and vinorelbine, synthesized from the monomeric alkaloid precursors, catharanthine and vindoline.

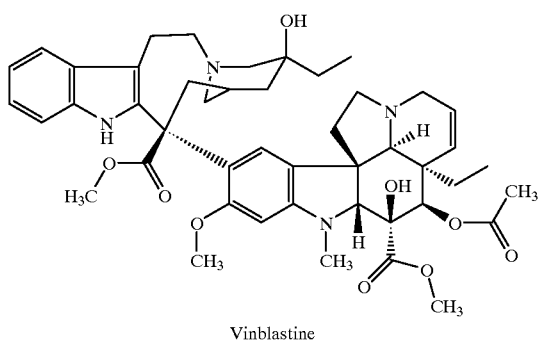

Vinblastine

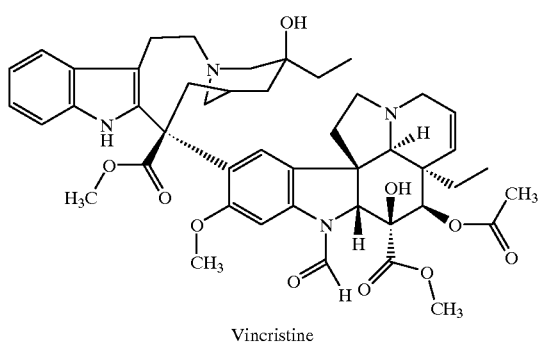

Vincristine

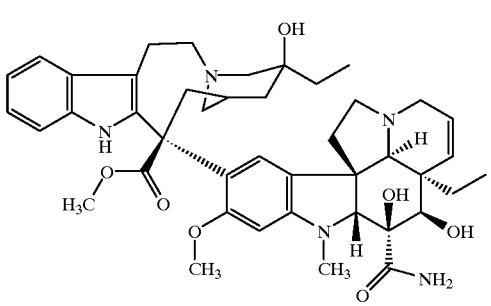

Vindesine

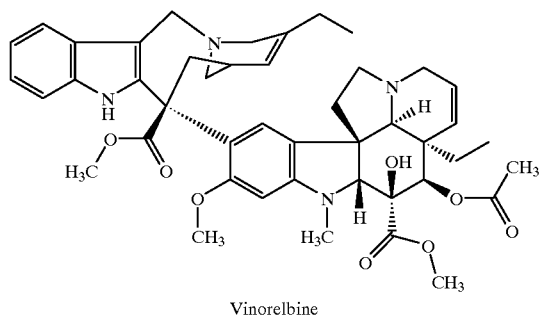

Vinorelbine

STRUCTURES OF THE VINCA ALKALOIDS USED IN CHEMOTHERAPY

In the context of our research studies directed toward obtaining novel derivatives of this family which might lead to novel applications in anticancer chemotherapy, we have adopted an original approach which consists in using the exceptional reactivity of superacid media, which is capable of inducing profound changes in these highly functionalized molecules.

We have thus already prepared a series of compounds difluorinated in position 20', which have hitherto been inaccessible by standard synthetic methods (patent FR 2,707,988 of Jul. 21, 1993, WO 95/03312), and whose pharmacological properties are particularly advantageous.

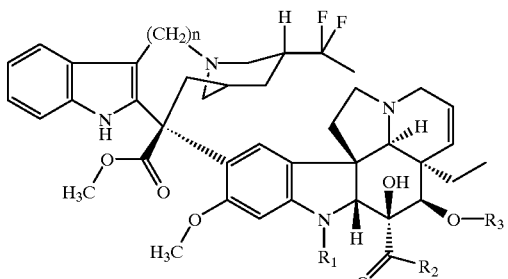

GENERAL FORMULA OF THE COMPOUNDS DESCRIBED IN PATENT FR 2,707,988

The application of this uncommon chemistry to complex molecules of this type has enabled us to prepare a novel family of halogenated compounds, which are also inaccessible by standard chemistry.

The subject of the present invention, carried out at the Pierre Fabre Research Center, is novel derivatives of Vinca alkaloids, a method for their preparation and their therapeutic application.

The compounds of the invention have the general formula 1, represented schematically below:

General formula 1

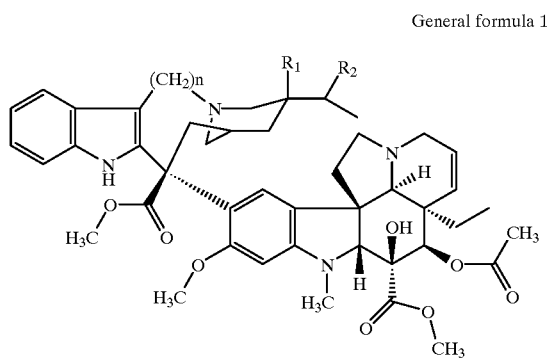

in which:
n=1 or 2,
$R_1$ represents a hydrogen or fluorine atom,
$R_2$ represents a chlorine atom.

The invention also relates to the salts of the compounds of general formula 1 with pharmaceutically acceptable inorganic or organic acids. The acid used may be, by way of non-limiting example, sulfuric acid or tartaric acid.

The invention relates both to the isomers corresponding to the R and S configurations of the 4' and 20' carbons of the compounds of general formula 1, and their mixtures in any proportion.

The derivatives of the invention are prepared by reaction of a compound of general formula 2 in superacid medium, obtained by mixing a strong Bronsted acid such as hydrofluoric acid, and a strong Lewis acid such as antimony pentafluoride, in the presence of a reagent which generates species of superelectrophilic type, according to the terminology proposed by G. Olah (*Ang. Chem. Int. Ed. Engl.*, 32, 767–88, 1993). This reagent can consist of a chloro derivative such as methylene chloride, chloroform, carbon tetrachloride, 2,2-dichloropropane or a mixture of these derivatives in all proportions.

The structure of the compounds of formula 2 is described below:

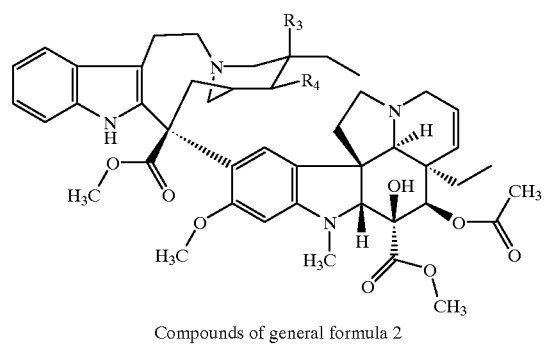

Compounds of general formula 2 in which:
$R_3$ represents a hydroxyl group and $R_4$ represents a hydrogen atom, in which case compound 2 corresponds to vinblastine,
or alternatively:
$R_3$ and $R_4$ form a double bond, in which case the compound of formula 2 corresponds to 3',4'-anhydrovinblastine.

The reactions in superacid medium are carried out in hydrofluoric acid-resistant containers such as Teflon® or a steel of suitable composition. The derivative of formula 2, in which $R_3$ and $R_4$ are defined as above, is dissolved in hydrofluoric acid or, in a chloro derivative defined as above acting as solvent, and added to the superacid mixture, which may optionally already contain a fraction of chloro derivative. This addition is carried out while maintaining the temperature of the medium at a chosen value, of between −80 and −30° C.

At low temperature and in the presence of methylene chloride or carbon tetrachloride, the compounds of formula 1 in which n=2, $R_1$=H and $R_2$=Cl are predominantly isolated. The compounds of formula 1 in which n=2, $R_1$=F and $R_2$=Cl are isolated from the same reaction medium in lower proportion. This is summarized in the scheme below:

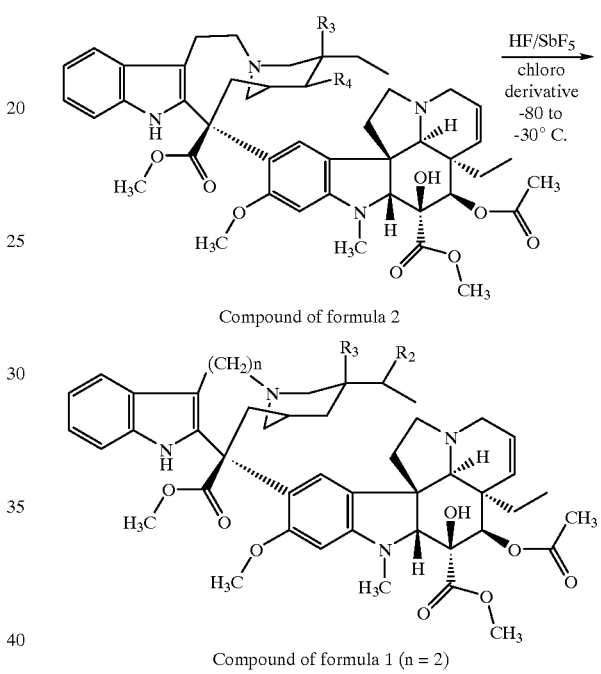

The derivatives of general formula 1, in which n=1, $R_1$ and $R_2$ being defined as above, are prepared by contracting ring C' (n=2→n=1) of the compounds of general formula 1 in which n=2, according to the methods described in the literature (*Eur. J. Med. Chem.*, 18, 419–24, 1983), in particular by the action of N-bromosuccinimide in methylene chloride in the presence of an acid such as trifluoroacetic acid and at a temperature below −10° C. After neutralization in basic medium, the 9'-bromoindolenine of the derivative of formula 1 in which n=2, a relatively unstable intermediate which is not isolated, undergoes a hydrolysis preferably in a mixture [methylene chloride: water:tetrahydrofuran], in the presence or absence of silver tetrafluoroborate ($AgBF_4$), at a temperature of between −10° C. and the reflux point of the solvent. The addition of $AgBF_4$, in catalytic or stoichiometric amount relative to compound 1 (n=2), makes, it possible to accelerate the course of the reaction, if this reaction is not complete after the neutralization step.

The major reaction product corresponds to the compound of formula 1 in which n=1. This reaction is represented schematically below:

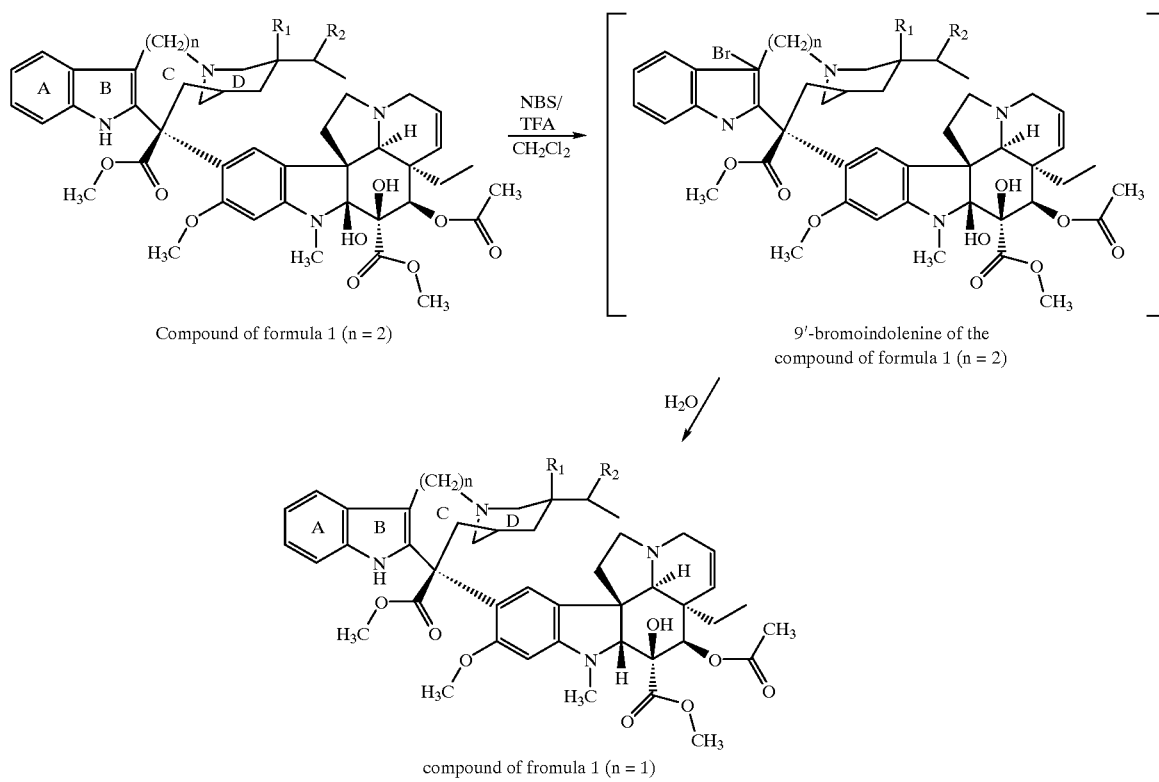

Compound of formula 1 (n = 2)

9'-bromoindolenine of the compound of formula 1 (n = 2)

compound of fromula 1 (n = 1)

A subject of the invention is also a novel process for the synthesis of 4'-deoxy-20',20'-difluorovinblastine, as well as 20',20'-difluoro-3',4'-dihydrovinorelbine or vinflunine, compounds claimed in patent FR 2,707,988 of 07.21.93 (WO 95/03312).

By modifying the operating conditions of the reaction in superacid medium using the compounds of formula 2 in which n=2, $R_3$ and $R_4$ being defined as above, 4'-deoxy-20', 20'-difluorovinblastine is preferentially obtained. These changes in operating conditions consist essentially in increasing the temperature (between −45 and −35° C.), extending the reaction time, or using a superelectrophile of different reactivity. In point of fact, we have shown, in a study of the reaction kinetics, that the compounds of formula 1 which can be isolated, in which n=2, $R_1$=H and $R_2$=Cl, which are predominant in the above case (41%), disappear at the expense of the product which is difluorinated in position 20' under these new conditions.

By optimizing the operating conditions, the yield for this difluorination reaction is better (50%) than that obtained by the process described in the patent cited above, which uses in particular N-bromosuccinimide (NBS) as electrophilic agent, since the yield indicated for the difluorination of vinorelbine in the presence of NBS is only 25%.

The compounds of general formula 2 are vinblastine when $R_3$=OH and $R_4$=H, and 3',4'-anhydrovinblastine when $R_3$ and $R_4$ together form a double bond. The derivative of formula 2 is dissolved in the chloro derivative, preferably chloroform or 2,2-dichloropropane, or a mixture containing chloroform or 2,2-dichloropropane, and added to the superacid medium, while maintaining the temperature of this medium between −45 and −35° C. The difluoro derivative, 4'-deoxy-20',20'-difluorovinblastine, thus constitutes the major final product of the reaction. Assaying by analytical HPLC indicates a proportion of this compound of about 50%.

This reaction is illustrated in the scheme below:

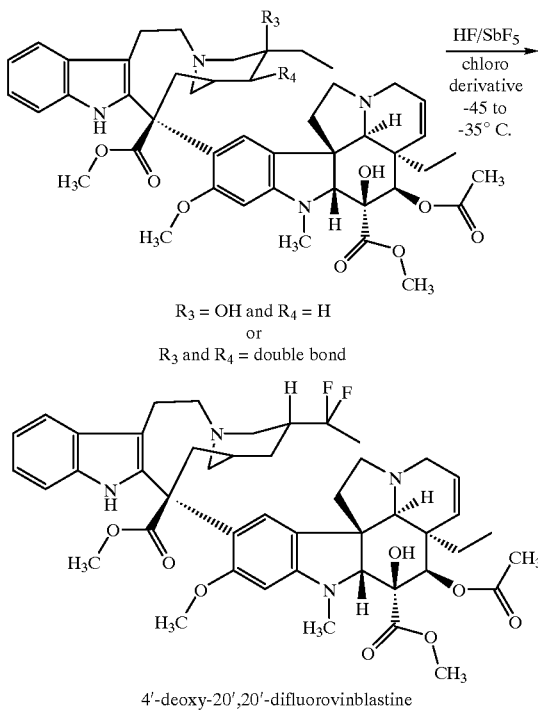

$R_3$ = OH and $R_4$ = H
or
$R_3$ and $R_4$ = double bond

4'-deoxy-20',20'-difluorovinblastine

Other agents which generate superelectrophilic ions, such as carbon tetrabromide $CBr_4$, dibromomethane $CH_2Br_2$ or boron tribromide $BBr_3$, also predominantly give 4'-deoxy-20',20'-difluorovinblastine.

This method thus constitutes a novel process for preparing 4'-deoxy-20',20'-difluorovinblastine, in a yield greater than that obtained by the prior art.

4'-Deoxy-20',20'-difluorovinblastine obtained according to this route can then undergo a contraction of its ring C' (n=2→n=1), as described above, by reaction with N-bromosuccinimide in methylene chloride in the presence of an acid such as trifluoroacetic acid at a temperature below −10° C. After neutralization in basic medium, the intermediate compound, 9'-bromoindolenine of 4'-deoxy-20',20'-difluorovinblastine, which is relatively unstable and not isolated, undergoes a hydrolysis preferably in a mixture [methylene chloride:water:tetrahydrofuran], in the presence or absence of tetrafluoroborate. In the same way as above, the addition of $AgBF_4$ makes it possible to increase the reaction speed.

The major compound obtained, in a yield of about 80%, corresponds to 20',20'-difluoro-3',4'-dihydrovinorelbine or vinflunine. The scheme below summarizes this reaction:

The examples which follow illustrate the invention without, however, limiting its scope. The spectroscopic characteristics confirm the structure of the compounds obtained according to the invention.

EXAMPLE 1:

20'-chloro-4'-deoxyvinblastine 1.

(n=2, $R_1$=H, $R_2$=Cl)

A solution of antimony pentafluoride (60 g; 0.28 mol) in 80 ml (4 mol) of anhydrous hydrofluoric acid is prepared in a 250 ml Teflon container and cooled to −60° C. With magnetic stirring, 1.63 ml (17 mmol) of carbon tetrachloride are then added thereto, followed by dropwise addition of a solution of 13.75 g (17 mmol) of 3',4'-anhydrovinblastine 2 (n=2, $R_3$ and $R_4$ forming a double bond) in 25 ml of methylene chloride, while ensuring that the temperature does not exceed −40° C. After 30 minutes, the reaction medium is poured very cautiously into 1.5 liters of an aqueous 3M suspension of $Na_2CO_3$ containing 200 ml of

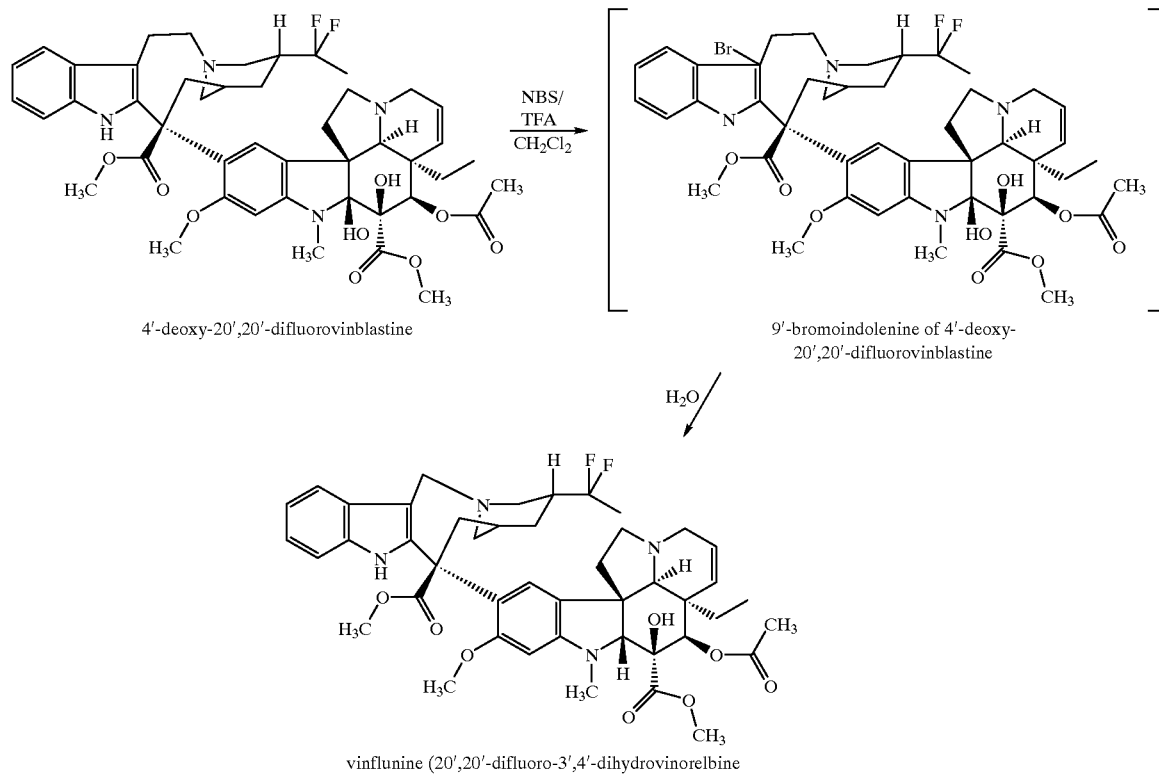

vinflunine (20',20'-difluoro-3',4'-dihydrovinorelbine)

This sequence of two steps thus constitutes a novel process for the synthesis of vinflunine, which is more advantageous than the previous one in the sense that:

1) the fluorination reaction in superacid medium is carried out using natural compounds such as vinblastine or 3',4'-anhydrovinblastine, which are directly accessible by extraction of the leaves of *Catharanthus roseus*, rather than from vinorelbine, which is a more expensive semisynthetic product,
2) the yield for the difluorination reaction by this novel process is about 50% as compared to 25% with the previous process,
3) the chromatographic purification of the compounds obtained, in particular 4'-deoxy-20',20'-difluorovinblastine, is less difficult than in the previous case.

methylene chloride. After separation of the phases by settling, the aqueous phase is extracted with 100 ml of methylene chloride. The organic phases are combined, washed with saturated NaCl solution, dried over $MgSO_4$ and evaporated.

Analysis by analytical HPLC of the residue recovered shows the presence of two close peaks integrating to a total of 41% (21 and 20%), noted as product of Example 1a and product of Example 1b in the tables describing the NMR spectra, corresponding to the two diastereoisomers at 20' of 20'-chloro-4'-deoxyvinblastine.

The purification is carried out by chromatography on a column of silica, and then by reverse-phase preparative HPLC.

The two diastereoisomers of 20'-chloro-4'-deoxyvinblastine separated are salified in ditartrate form by addition of two (molar) equivalents of tartaric acid in water, and lyophilized.

$C_{46}H_{57}ClN_4O_8$, $2(C_4H_6O_6)$: 1129.62; Melting point: >260° C; IR(KBr): 3448.17 1736.05 1615.36 1459.86 1372.51 1231.89 1121.18 1067.54 $cm^{-1}$; Mass spectrum (D/CI $NH_3$): $MH^+$=829.4.

EXAMPLE 2:
20'-chloro-4'-deoxyvinblastine 1.
(n=2, $R_1$=H, $R_2$=Cl)

This compound is obtained according to the procedure described in Example 1, replacing the 3',4'-anhydrovinblastine 2 (n=2, $R_3$ and $R_4$ forming a double bond) with vinblastine 2 (n=2, $R_3$=OH, $R_4$=H).

The physicochemical and spectroscopic characteristics of the products isolated are identical to those of the compounds obtained in Example 1.

EXAMPLE 3:
20'-chloro-4'-deoxy-4'-fluorovinblastine 1.
(n=2, $R_1$=F, $R_2$=Cl)

This compound is isolated from the reaction mixture obtained in Example 1 or in Example 2, from other less polar fractions derived from the chromatography on a column of silica. The final purification is carried out by reverse-phase preparative HPLC.

The 20'-chloro-4'-deoxy-4'-fluorovinblastine is salified in ditartrate form by addition of two (molar) equivalents of tartaric acid in water, and lyophilized.

$C_{46}H_{56}ClFN_4O_8$, $2(C_4H_6O_6)$: 1147.61; Melting point: >260° C.; IR(KBr): 3470.13 2951.45 1735.92 1616.62 1458.44 1371.64 1228.52 1040.10 743.07 $cm^{-1}$; Mass spectrum (D/CI $NH_3$): $MH^+$=847.4.

EXAMPLE 4:
20'-chloro-3',4'-dihydrovinorelbine 1.
(n=1, $R_1$=H, $R_2$=Cl)

900 mg (1.08 mmol) of 20'-chloro-4'-deoxyvinblastine 1 (n=2, $R_1$=H, $R_2$=Cl), isolated according to Example 1, are dissolved in 5 ml of methylene chloride containing 95 μl (1.2 mmol) of trifluoroacetic acid, cooled to −45° C. The assembly is placed under shelter from light and 193 mg (1.08 mmol) of N-bromosuccinimide are added as a solution in 2 ml of $CH_2Cl_2$ and 95 μl (1.2 mmol) of TFA, and the mixture is left stirring for 30 minutes. The mixture is then neutralized by addition of 5 ml of saturated $NaHCO_3$ solution, immediately followed by a solution of 211 mg (1.08 mmol) of silver tetrafluoroborate in a mixture of 5 ml of tetrahydrofuran and 2 ml of water. The resulting mixture is allowed to return to room temperature with magnetic stirring for about two hours.

After filtration, the organic phase is separated out and washed with twice 10 ml of water and then 10 ml of saturated NaCl solution. After drying over $MgSO_4$, the solution is evaporated and the residue is purified by chromatography on a column of silica, and then by reverse-phase preparative HPLC.

$C_{45}H_{55}ClN_4O_8$: 815.41; IR(KBr): 3446 2950 1740.89 1459.16 1246.59 1200.65 1042 $cm^{-1}$; Mass spectrum (D/CI $NH_3$): $MH^+$=815.4.

EXAMPLE 5:
20'-chloro-3',4'-dihydro-4'-fluorovinorelbine 1.
(n=1, $R_1$=F, $R_2$=Cl)

This compound is obtained according to the procedure described in Example 4, replacing the 20'-chloro-4'-deoxyvinblastine with 20'-chloro-4'-deoxy-4'-fluorovinblastine 1 (n=2, $R_1$=F, $R_2$=Cl). The 20'-chloro-3',4'-dihydro-4'-fluorovinorelbine is purified by chromatography under identical conditions.

$C_{45}H_{54}ClFN_4O_8$: 833.40; IR(KBr): 3446.83 2950.98 1742.73 1617.73 1457.36 1234.38 1042.23 996.50 742.15 $cm^{-1}$; Mass spectrum (D/CI $NH_3$): $MH^+$=833.5.

The chemical shifts of characteristic protons of the new structures prepared above are collated in the table below:

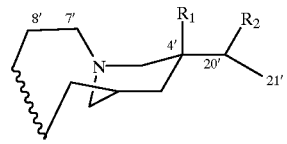

| Hydrogen atom | Product of example | | | |
|---|---|---|---|---|
| | 1a and 1b | 3 | 4 | 5 |
| $H_{4'}$ | 1.95 (m, 1H) | — | 1.90 (m, 1H) | — |
| $H_{7'}$ | 3.1–3.3 (m, 2H) | 3.1 (m, 1H) 3.3 (m, 1H) | 4.32 (d, 1H) 4.46 (d, 1H) | 4.38 (d, 1H) 5.07 (d, 1H) |
| $H_{8'}$ | 3.1–3.25 (m, 2H) | 3.05 (m, 1H) 3.45 (m, 1H) | — | — |
| $H_{20'}$ | 3.68 (m, 1H) | 3.80 (m, 1H) | 3.80 (m, 1H) | 3.93 (m, 1H) |
| $H_{21'}$ | 1.50 (d, 3H) | 1.44 (d, 3H) | 1.50 (d, 3H) | 1.57 (d, 3H) |

The description of the $^{13}C$ NMR spectra of the new products obtained according to the above examples is detailed in the table below:

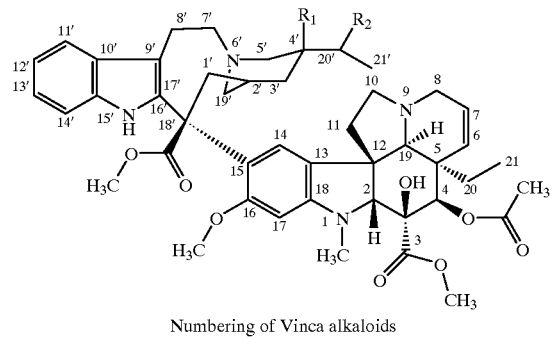

Numbering of Vinca alkaloids (according to the I.U.P.A.C. recommendations)

| Example Carbon No. | 1a | 1b | 3 | 4 | 5 |
|---|---|---|---|---|---|
| 1 | N | N | N | N | N |
| 2 | 83.348 | 83.348 | 82.72 | 83.5 | 83.26 |
| 3 | 79.71 | 79.71 | 79.01 | 80.07 | 79.74 |
| 4 | 76.496 | 76.466 | 75.78 | 76.78 | 76.46 |
| 5 | 42.69 | 42.69 | 42.04 | 42.95 | 42.66 |
| 6 | 130.04 | 130.01 | 129.41 | 130.31 | 130.08 |
| 7 | 124.583 | 124.583 | 123.89 | 124.94 | 124.54 |
| 8 | 50.27 | 50.209 | 49.64 | 50.75 | 50.49 |
| 9 | N | N | N | N | N |
| 10 | 50.27 | 50.209 | 49.64 | 50.55 | 50.38 |
| 11 | 44.6 | 44.63 | 44.03 | 44.8 | 44.48 |
| 12 | 53.332 | 53.332 | 52.63 | 53.55 | 53.23 |
| 13 | 122.673 | 122.733 | 122.07 | 123 | 122.64 |
| 14 | 123.431 | 123.461 | 122.87 | 123.37 | 123.17 |
| 15 | 121.066 | 121.036 | 120.48 | 120.02 | 120.84 |
| 16 | 158.086 | 158.056 | 157.52 | 158.3 | 158.12 |
| 17 | 94.142 | 94.142 | 93.63 | 94.19 | 94.01 |

-continued

| Example Carbon No. | 1a | 1b | 3 | 4 | 5 |
|---|---|---|---|---|---|
| 18 | 152.75 | 152.719 | 152.07 | 153.01 | 152.65 |
| 19 | 65.369 | 65.399 | 64.83 | 65.64 | 65.45 |
| 20 | 30.835 | 30.835 | 30.17 | 31 | 30.71 |
| 21 | 8.368 | 8.399 | 7.72 | 8.42 | 8.1 |
| 22 | 38.415 | 38.385 | 37.76 | 38.65 | 38.45 |
| 23 | 171.669 | 171.669 | 171.06 | 171.95 | 171.69 |
| 24 | 52.271 | 52.271 | 51.57 | 52.51 | 52.23 |
| 25 | 55.849 | 55.849 | 55.29 | 56.04 | 55.49 |
| 26 | 170.941 | 170.941 | 170.13 | 171.22 | 170.88 |
| 27 | 21.193 | 21.193 | 20.45 | 21.45 | 21.15 |
| 1' | 33.594 | 33.594 | 33 | 32.24 | 33.59 |
| 2' | 30.016 | 30.077 | 28.56 | 29.67 | 29.71 |
| 3' | 34.867 | 35.929 | 35.4 | 34.85 | 35.4 |
| 4' | 38.779 | 59.355 | 92.52 | 31 | 95.92 |
| 5' | 56.819 | 57.243 | 58.43 | 55 | 56.7 |
| 6' | N | N | N | N | N |
| 7' | 56.819 | 56.788 | 55.4 | 47.38 | 46.98 |
| 8' | 28.986 | 29.076 | 27.69 | Absent | Absent |
| 9' | 117.064 | 117.185 | 116.07 | 110.76 | 111.68 |
| 10' | 129.252 | 129.282 | 128.72 | 129.09 | 128.7 |
| 11' | 118.337 | 118.398 | 117.7 | 118.77 | 118.23 |
| 12' | 118.883 | 118.913 | 118.2 | 120.01 | 119.56 |
| 13' | 122.339 | 122.37 | 121.63 | 123.04 | 122.46 |
| 14' | 110.575 | 110.545 | 109.9 | 110.76 | 110.52 |
| 15' | 135.073 | 135.073 | 134.45 | 134.98 | 134.69 |
| 16' | N | N | N | N | N |
| 17' | 130.617 | 130.495 | 130.49 | 133.3 | 133.43 |
| 18' | 55.454 | 55.424 | 54.95 | 55.04 | 55.77 |
| 19' | 47.42 | 47.45 | 46.11 | 48.6 | 47.04 |
| 20' | 62.155 | 62.428 | 60.7 | 62.7 | 61.24 |
| 21' | 22.406 | 22.649 | 18.5 | 23.05 | 18.64 |
| 22' | 174.883 | 174.883 | 174.17 | 175 | 175 |
| 23' | 52.45 | 52.453 | 51.7 | 52.96 | 52.62 |

$^{13}$C NMR Characteristics of the Compounds Prepared

EXAMPLE 6:
4'-deoxy-20',20'-difluorovinblastine

A solution of antimony pentafluoride (750 g; 3.45 mol) in 500 ml (25 mol) of anhydrous hydrofluoric acid is prepared in a 6 liter Astelloy steel reactor and is cooled to −45° C. A solution of 107 g (0.12 mol) of 3',4'-anhydrovinblastine dihydrochloride dissolved in 250 ml of chloroform is added thereto over 30 minutes, while keeping the temperature at −35° C. The mixture is left stirring for an additional 30 minutes at this temperature. 200 ml of acetone are then introduced over 30 minutes at −30° C., followed by 150 ml of water over 15 minutes at −25° C. While allowing the temperature to rise to 20° C., 900 ml of methylene chloride are added, followed by 650 ml of water. After separation of the phases by settling, the aqueous phase is extracted with 100 ml of methylene chloride. The organic phases are combined and neutralized at a temperature below 20° C. with 600 ml of 10% KOH. After separation of the phases by settling, the organic phase is stirred overnight in the presence of 800 ml of 10% aqueous ammonia, followed by washing twice with 400 ml of water, drying over MgSO$_4$ and then evaporation.

The purification is carried out by chromatography on a column of silica eluted with a toluene/acetone mixture (65/35). The residue obtained after evaporation is dissolved in 80 ml of methylene chloride and precipitated by addition of 350 ml of isopropyl ether. After filtration, 41 g (40%) of 4'-deoxy-20',20'-difluorovinblastine are recovered.

The physicochemical and spectroscopic characteristics of the compound isolated are identical to those of the product obtained according to the process described in patent FR 2,707,988 of Jul. 21, 1993 (WO 95/03312) U.S. Pat. No. 5,620,985.

EXAMPLE 7:
4'-deoxy-20',20'-difluorovinblastine

A solution of antimony pentafluoride (8.6 g; 40 mmol) in 7.2 ml (360 mmol) of anhydrous hydrofluoric acid is prepared in a 125 ml Teflon container and cooled to −45° C. With magnetic stirring, 0.94 ml (9 mmol) of 2,2-dichloropropane is then added thereto, followed by dropwise addition of a solution of 0.71 g (0.9 mmol) of 3',4'-anhydrovinblastine 2 (n=2, R$_3$ and R$_4$ forming a double bond) in 3.6 ml of hydrofluoric acid, while ensuring that the temperature does not exceed −35° C. After 25 minutes, the reaction medium is poured very cautiously into 300 ml of aqueous 3M Na$_2$CO$_3$ solution. After separation of the phases by settling, the aqueous phase is extracted with 50 ml of methylene chloride. The organic phases are combined, washed with saturated NaCl solution, dried over MgSO$_4$ and evaporated.

The residue contains 46% of 4'-deoxy-20',20'-difluorovinblastine, which is identical to the product obtained according to the process described in patent FR 2,707,988 of Jul. 21, 1993 (WO 95/03312).

EXAMPLE 8:
4'-deoxy-20',20'-difluorovinblastine

This compound is obtained according to the procedure described in Example 7, replacing the 2,2-dichloropropane with carbon tetrabromide CBr$_4$ during the treatment in superacid medium.

The physicochemical and spectroscopic characteristics of the compound isolated are identical to those of the product obtained according to the process described in patent FR 2,707,988 of Jul. 21, 1993 (WO 95/03312) U.S. Pat. No. 5,620,985.

EXAMPLE 9:
4'-deoxy-20',20'-difluorovinblastine

This compound is obtained according to the procedure described in Example 7, replacing the 2,2-dichloropropane with boron tribromide BBr$_3$ during the treatment in superacid medium.

The physicochemical and spectroscopic characteristics of the compound isolated are identical to those of the product obtained according to the process described in patent FR 2,707,988 of Jul. 21, 1993 (WO 95/03312) U.S. Pat. No. 5,620,985.

EXAMPLE 10:
4'-deoxy-20',20'-difluorovinblastine

This compound is obtained according to the procedure described in Example 7, replacing the 2,2-dichloropropane with dibromomethane CH$_2$Br$_2$ during the treatment in superacid medium.

The physicochemical and spectroscopic characteristics of the compound isolated are identical to those of the product obtained according to the process described in patent FR 2,707,988 of Jul. 21, 1993 (WO 95/03312) U.S. Pat. No. 5,620,985.

EXAMPLE 11:

20',20'-difluoro-3',4'-dihydrovinorelbine (vinflunine)

90 g (0.108 mol) of 4'-deoxy-20',20'-difluorovinblastine are dissolved in 800 ml of methylene chloride and cooled to −45° C., to which solution are added 10.4 ml (0.135 mol) of trifluoroacetic acid. The assembly is placed under shelter from light and a solution composed of 19.3 g (0.108 mol) of N-bromosuccinimide in a mixture of 200 ml of methylene chloride and 10.4 ml (0.135 mol) of trifluoroacetic acid is added thereto over about 30 minutes, while taking care to ensure that the temperature of the medium does not rise above −45° C.

After 30 minutes, the mixture is neutralized by addition of 300 ml of 10% NaHCO$_3$ solution, followed immediately by a solution of 23.4 g (0.12 mol) of silver tetrafluoroborate in a mixture of 300 ml of tetrahydrofuran and 100 ml of water. The resulting mixture is allowed to return to room temperature with stirring for about 2 hours.

After filtration, the organic phase is separated out and washed with twice 150 ml of water. After drying over MgSO$_4$, the solution is evaporated and the residue is dissolved in 500 ml of methanol and then evaporated in order to obtain 97 g of dry residue, containing 88% of 20',20'-difluoro-3',4'-dihydrovinorelbine (vinflunine).

The purification is carried out by preparative HPLC on C$_{18}$ grafted silica (particle size 15–25μ), with an eluent composed of water, acetic acid, ammonium acetate, methanol and acetonitrile. The purified fractions are concentrated to half their volume, brought to pH=7 and extracted twice with toluene. The organic phase is washed three times with distilled water and then assayed by analytical HPLC.

The vinflunine, in solution in toluene, is extracted with an aqueous solution containing exactly two (molar) equivalents of tartaric acid. The aqueous phase is then lyophilized in order to obtain vinflunine ditartrate.

The physicochemical and spectroscopic characteristics of the compound isolated are identical to those of the product obtained according to the process described in patent FR 2,707,988 of Jul. 21, 1993 (WO 95/03312) U.S. Pat. No. 5,620,985.

As with the antitumor alkaloids of Catharanthus roseus, the compounds prepared according to the invention are "poisons of the mitotic spindle".

This property was confirmed by measuring the inhibition of the polymerization of tubulin into microtubules in the presence of the compounds of the invention, according to the method described by R. C. Weisenberg (*Science* 177, 1196–7, 1972). The results are expressed in terms of IC$_{50}$, which corresponds to the concentration of compound which brings about a 50% inhibition of the polymerization. This phenomenon is readily monitored and quantified by means of the changes in optical density.

By way of example, the table below shows the results obtained with two derivatives prepared according to the invention:

| Product | IC$_{50}$ (μM) |
| --- | --- |
| Example 1 | 1.99 |
| Example 3 | 1.54 |
| Vinorelbine | 1.70 |

Given this characteristic pharmacological property of the Vinca alkaloids, the compounds of the present invention can be used in anticancer chemotherapy.

The pharmaceutical preparations containing these active principles can be formulated for oral, intravenous or subcutaneous administration, in a conventional manner, which is well known to those skilled in the art.

What is claimed is:

1. An antimitotic derivative of a Vinca alkaloid selected from those corresponding to the formula below:

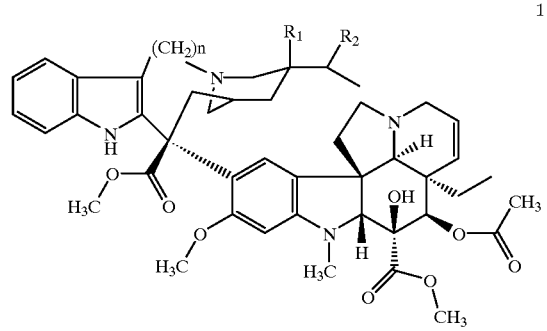

in which:

n=1 or 2,

R$_1$ represents a hydrogen atom or a fluorine atom,

R$_2$ represents a chlorine atom, a salt thereof with a therapeutically-acceptable inorganic or organic acid, or a diastereomer thereof.

2. A compound of claim 1, selected from the group consisting of 20'-chloro-4'-deoxy-4'-fluorovinblastine:

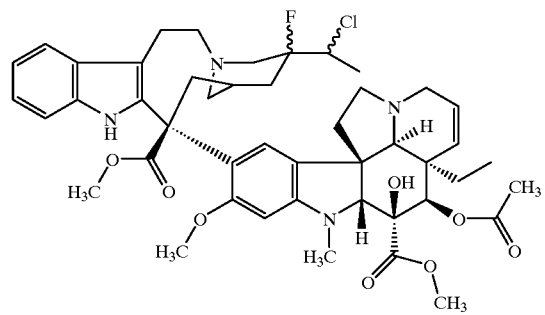

20'-chloro-4'-deoxyvinblastine:

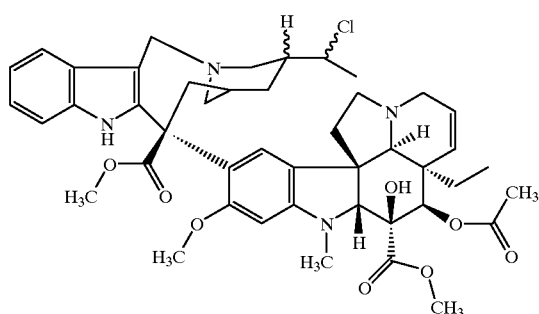

20'-chloro-3',4'-dihydrovinorelbine:

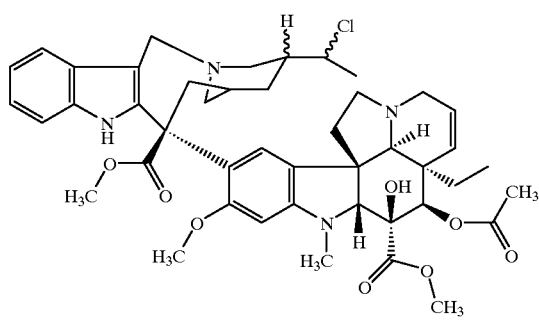

and 20'-chloro-3',4'-dihydro-4'-fluorovinorelbine:

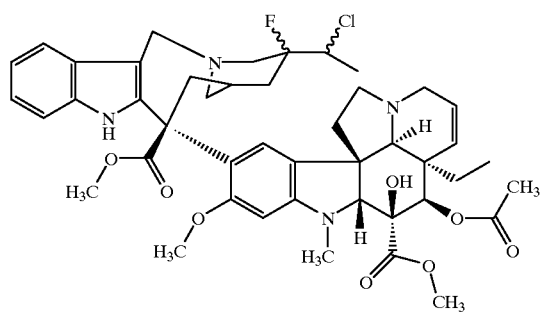

3. Process for preparing a compound according to claim 1 wherein a compound of formula 2 is reacted in superacid medium, obtained by combining a Bronsted acid, and a Lewis acid, in the presence of a chloro compound which generates superelectrophilic ions, according to the scheme:

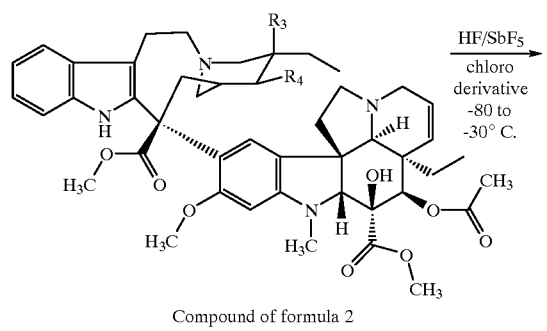

Compound of formula 2

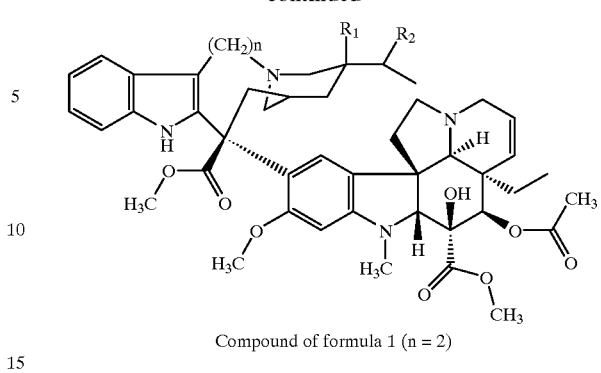

Compound of formula 1 (n = 2)

4. Process of claim 3, wherein the reaction of a compound of formula 2 in superacid medium is carried out at a temperature between −80 and −30° C.

5. Process of claim 3, wherein the chloro compound which generates superelectrophilic ions is chosen from:

methylene chloride, chloroform, carbon tetrachloride, and 2,2-dichloropropane, or a mixture of these compounds.

6. Process of claim 3 wherein the chloro compound which generates superelectrophilic ions, which is used to obtain the compound of formula 1 in which n=2, is methylene chloride, carbon tetrachloride, or a mixture of these compounds.

7. Process for preparing a compound according to claim 1, wherein a compound of formula 1 in which n=2, $R_1$ and $R_2$ being defined as in claim 1, is reacted with a halogenating agent, in a chlorinated solvent and in the presence of an acid at a temperature below −10° C., leading to the corresponding 9'-bromoindolenine, which intermediate is not isolated.

8. Process for preparing a compound of claim 1, wherein a reaction mixture containing a 9'-bromoindolenine of formula 1 in which n=2 is neutralized with a basic medium, followed by hydrolysis in the presence or absence of silver tetrafluoroborate at a temperature between −10° C. and the reflux point of the solvent, in order to obtain the compound of formula 1 in which n=1, according to the scheme below:

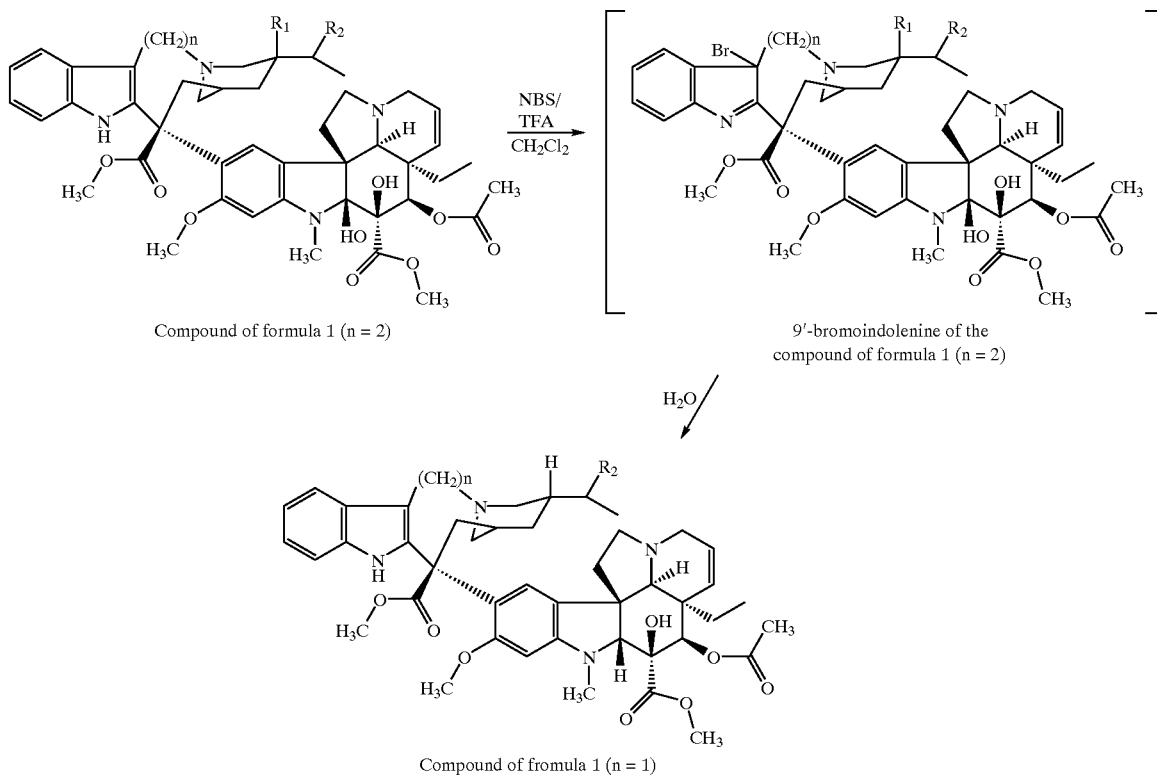

Compound of formula 1 (n = 2)

9'-bromoindolenine of the compound of formula 1 (n = 2)

Compound of fromula 1 (n = 1)

9. Pharmaceutical composition which comprises, as active principle, at least one compound according to claim 1, combined with a pharmaceutically acceptable vehicle.

10. Pharmaceutical composition which comprises as active principle, at least one compound according to claim 2 combined with a pharmaceutically acceptable vehicle.

11. A method for the treatment of cancer responsive to a vinca alkaloid in a living animal body comprising the step of administering to the living animal body in need thereof an effective anti-cancer amount of a compound of claim 1.

12. A method for the treatment of cancer responsive to a vinca alkaloid in a living animal body comprising the step of administering to the living animal body in need thereof an effective anti-cancer amount of a compound of claim 2.

13. The process of claim 8, wherein the hydrolysis is effected using a mixture of methylene chloride, water, and tetrahydrofuran.

14. The process of claim 7, wherein the halogenating agent is N-bromosuccinimide, the chlorinated solvent is methylene chloride, and the acid is trifluoroacetic acid.

15. Process of claim 5, wherein the chloro compound which generates superelectrophilic ions, which is used to obtain the compound of formula 1 in which n=2, is methylene chloride, carbon tetrachloride, or a mixture of these compounds.

16. The process of claim 3, wherein the Bronsted acid is hydrofluoric acid HF and the Lewis acid is antimony pentafluoride $SbF_5$.

* * * * *

UNITED STATES PATENT AND TRADEMARK OFFICE
CERTIFICATE OF CORRECTION

PATENT NO. : 6,127,377
DATED : October 3, 2000
INVENTOR(S) : Duflos et al.

It is certified that error appears in the above-identified patent and that said Letters Patent is hereby corrected as shown below:

Title page,
Item [73], Assignee, please delete "Adir et Compagnie", Courbevoie, France and insert -- Pierre Fabre Medicament, France --.

Signed and Sealed this

Ninth Day of April, 2002

Attest:

JAMES E. ROGAN
Director of the United States Patent and Trademark Office

*Attesting Officer*

UNITED STATES PATENT AND TRADEMARK OFFICE
CERTIFICATE OF CORRECTION

PATENT NO.     : 6,127,377
DATED          : October 3, 2000
INVENTOR(S)    : Alain Duflos et al.

It is certified that error appears in the above-identified patent and that said Letters Patent is hereby corrected as shown below:

<u>Columns 17 and 18,</u>
"Compound of fromula 1 (n = 1)" should read -- Compound of formula 1 (n = 1) --.

<u>Columns 17 and 18,</u>
Formula;

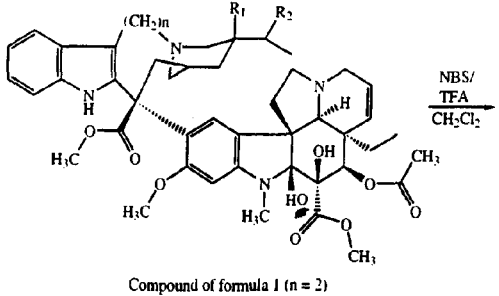

Compound of formula 1 (n = 2)

should be

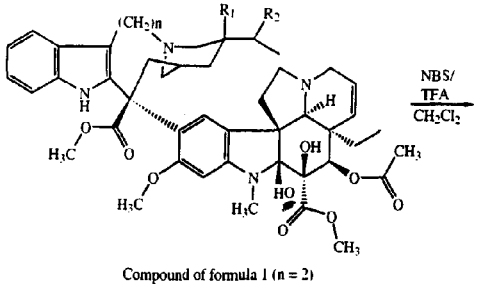

Compound of formula 1 (n = 2)

UNITED STATES PATENT AND TRADEMARK OFFICE
CERTIFICATE OF CORRECTION

PATENT NO.   : 6,127,377
DATED        : October 3, 2000
INVENTOR(S)  : Alain Duflos et al.

It is certified that error appears in the above-identified patent and that said Letters Patent is hereby corrected as shown below:

Column 17 and 18 cont'd,
Formula;

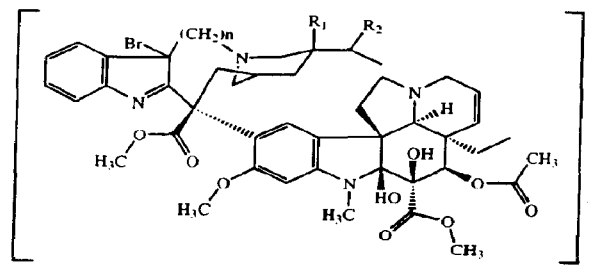

9'-bromoindolenine of the
compound of formula 1 (n = 2)

Should be

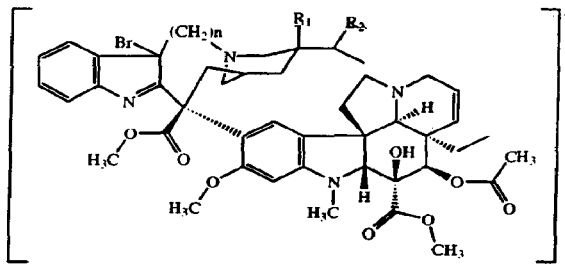

9'-bromoindolenine of the
compound of formula 1 (n = 2)

Formula;

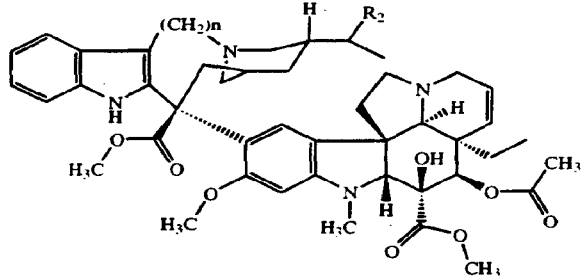

Compound of fromula 1 (n = 1)

UNITED STATES PATENT AND TRADEMARK OFFICE
CERTIFICATE OF CORRECTION

PATENT NO.    : 6,127,377
DATED         : October 3, 2000
INVENTOR(S)   : Alain Duflos et al.

It is certified that error appears in the above-identified patent and that said Letters Patent is hereby corrected as shown below:

Columns 17 and 18 cont'd,
Should be

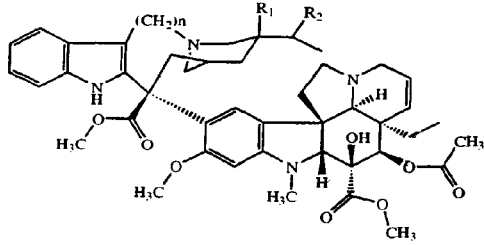

Compound of fromula 1 (n = 1)

Signed and Sealed this

Twenty-ninth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,127,377
DATED         : October 3, 2000
INVENTOR(S)   : Alain Duflos et al.

It is certified that error appears in the above-identified patent and that said Letters Patent is hereby corrected as shown below:

Columns 17 and 18,
"Compound of fromula 1 (n = 1)" should read -- Compound of formula 1 (n = 1) --.

Columns 17 and 18,
Formula;

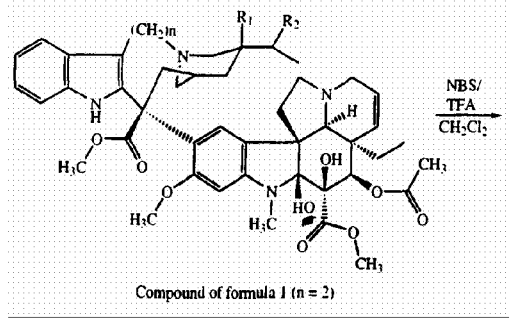

should be

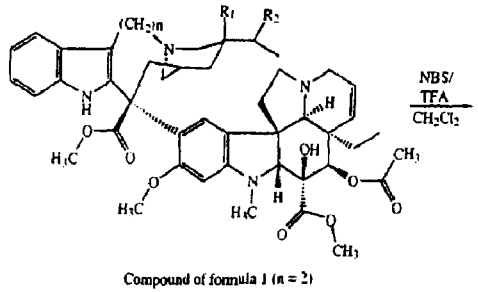

UNITED STATES PATENT AND TRADEMARK OFFICE
CERTIFICATE OF CORRECTION

PATENT NO. : 6,127,377  
DATED : October 3, 2000  
INVENTOR(S) : Alain Duflos et al.

Page 2 of 3

It is certified that error appears in the above-identified patent and that said Letters Patent is hereby corrected as shown below:

Column 17 and 18 cont'd,
Formula;

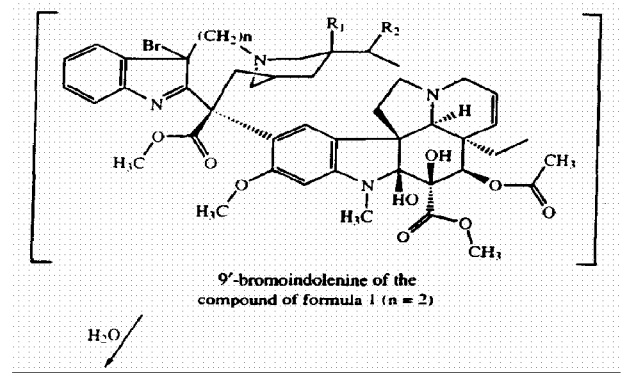

Should be

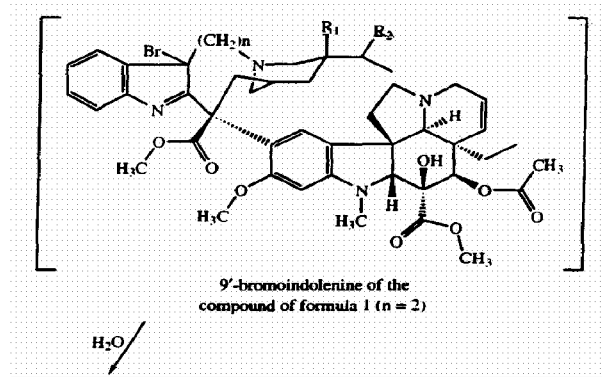

Formula;

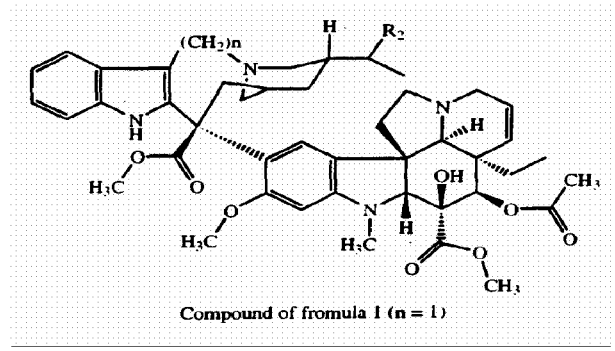

UNITED STATES PATENT AND TRADEMARK OFFICE
CERTIFICATE OF CORRECTION

PATENT NO.    : 6,127,377
DATED         : October 3, 2000
INVENTOR(S)   : Alain Duflos et al.

It is certified that error appears in the above-identified patent and that said Letters Patent is hereby corrected as shown below:

Columns 17 and 18 cont'd,
Should be

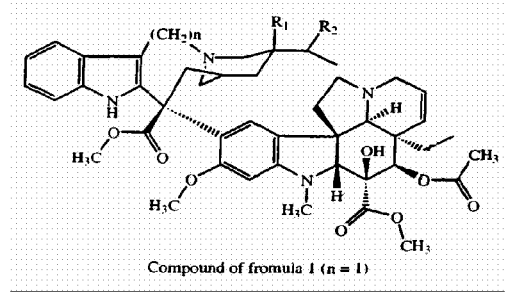

This certificate supersedes Certificate of Correction issued July 29, 2003.

Signed and Sealed this

Thirtieth Day of March, 2004

JON W. DUDAS
*Acting Director of the United States Patent and Trademark Office*